(12) United States Patent  
Camrud et al.

(10) Patent No.: US 6,709,449 B2  
(45) Date of Patent: Mar. 23, 2004

(54) STENT TREATMENT APPARATUS AND METHOD

(75) Inventors: Allan R. Camrud, Rochester, MN (US); Atoni Bayes-Genis, Barcelona (ES); Robert S. Schwartz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 113 days.

(21) Appl. No.: 09/759,906

(22) Filed: Jan. 12, 2001

(65) Prior Publication Data

US 2002/0138126 A1 Sep. 26, 2002

(51) Int. Cl.⁷ .................................................. A61F 2/06
(52) U.S. Cl. ....................... 623/1.11; 137/12; 15/104.03
(58) Field of Search ...................... 15/104.03; 623/1.11; 137/12

(56) References Cited

U.S. PATENT DOCUMENTS

| | | | | |
|---|---|---|---|---|
| 5,195,980 A | * | 3/1993 | Catlin | 604/167.04 |
| 5,639,274 A | * | 6/1997 | Fischell et al. | 604/96.01 |
| 5,681,322 A | * | 10/1997 | Hartigan, Jr. | 606/108 |
| 5,895,376 A | * | 4/1999 | Schwartz et al. | 604/256 |
| 6,010,530 A | | 1/2000 | Goicoechea | |
| 6,022,336 A | | 2/2000 | Zadno-Azizi et al. | |
| 6,096,027 A | | 8/2000 | Layne | |
| 6,168,579 B1 | * | 1/2001 | Tsugita | 604/96.01 |

OTHER PUBLICATIONS

Assoian, R. et al., "Expression and Secretion of Type β Transforming Growth Factor by Activated Human Macroph ages", *Proc. Natl. Acad. Sci. USA*, vol. 84, No. 17, pp. 6020–6024 (Sep. 1987).

Barron, M.K. et al., "Intimal Hyperplasia After Balloon Injury Is Attenuated by Blocking Selectins", *Circulation*, vol. 96, No. 10, pp. 3587–3592 (Nov. 18, 1997).

Cox, D. et al., "Effect of Local Delivery of Heparin and Methotrexate on Neointimal Proliferation in Stented Porcine Coronary Arteries", *Coronary Artery Disease*, vol. 3, no. 3, pp. 237–248 (Mar. 1992).

Farb, A. et al., "Pathology of Acute and Chronic Coronary Stenting in Humans", *Circulation*, vol. 99, No. 1, pp. 44–52 (Jan. 5/12, 1999).

Hardhammar, P.A. et al., "Reduction in Thrombotic Events With Heparin–Coated Palmaz–Schatz Stents in Normal Porcine Coronary Arteries", *Circulation*, vol. 93, No. 3, pp. 423–430 (Feb. 1, 1996).

Jacobs, A., "Coronary Stents—Have They Fulfilled Their Promise?", *N. eng. J. Med.*, vol. 341, No. 25, pp. 2005–2006 (Dec. 16, 1999).

(List continued on next page.)

Primary Examiner—Paul B. Prebilic  
(74) *Attorney, Agent, or Firm*—Merchant & Gould P.C.

(57) ABSTRACT

Manual stent manipulation before implantation results in foreign body contamination and increased neointimal hyperplasia. Rinsing commercially available sterile stents with high pressure immediately before implantation eliminates residual surface stent contaminants and reduces inflammation elicited by stent struts. Ex-vivo stent expansion and surface analysis revealed that rinsed stents had fewer surface contaminants than untouched or handled stents. In a porcine stent restenosis model, rinsed stents elicited less inflammation and less neointimal hyperplasia at one month than handled and untouched stents. Pressure-rinsing of coronary stents immediately before implantation reduces inflammation and neointimal hyperplasia.

8 Claims, 12 Drawing Sheets

OTHER PUBLICATIONS

Jung, F. et al., "Effect of Crimping on the Contamination of Coronary Stents", *European Heart Journal*, vol. 20, No. 8, pp. 628 (Apr. 1999).

Karas, S.P. et al., "Coronary Intimal Proliferation After Balloon Injury and stenting in Swine: An Animal Model of Restenosis", *J. Am. Coll. Cardiol.*, vol. 20, No.1, pp. 467–474 (Jul. 1992).

Kornowski, R. et al., "In–Stent Restenosis: Contributions of Inflammatory responses and Arterial Injury to Neointimal Hyperplasia", *J. Am. Coll. Cardiol.*, vol. 31, No. 1, pp. 224–230 (Jan. 1998).

Kornowski, R. et al., "Granulomatous 'foreign body reactions' contribute to exaggerated in–stent restenosis", *Coronary Artery Dis.*, vol. 10, No. 1, pp. 9–14 (1999).

Lucas, A. et al., "Virus–Encoded Serine Proteinase Inhibitor SERP–1 Inhibits Atherosclerotic Plaque Development After Balloon Angioplasty", *Circulation*, vol. 94, No. 11, pp. 2890–2900 (Dec. 1, 1996).

McKenna, C.J. et al., "Selective $ET_A$ Receptor Antagonism Reduces Neointimal Hyperplasia in a Porcine Coronary Stent Model", *Circulation*, vol. 97, No. 25, pp. 2551–2556 (Jun. 30, 1998).

Moreno, P.R. et al., "Macrophage Infiltration Predicts Restenosis After Coronary Intervention in Patients With Unstable Angina", *Circulation*, vol. 94, No. 12, pp. 3098–3102 (Dec. 15, 1996).

Peri, G. et al., "Cytotoxicity of Activated Monocytes on Endothelial Cells", *J. Immunol.*, vol. 144, No. 4, pp. 1444–1448 (Feb. 15, 1990).

Pizzoferrato, A. et al., "The Effect of Injection of Powdered Biomaterials on Mouse Peritoneal Cell Populations", *J. Biomed Materials Research*, vol. 21, No. 3, pp. 419–428 (Mar. 1987).

Rogers, C. et al., "Endovascular Stent Design Dictates Experimental Restenosis and Thrombosis", *Circulation*, vol. 91, No. 12, pp. 2995–3001 (Jun. 15, 1995).

Rogers, C. et al., "A mAb to the $\beta_2$–leukocyte integrin Mac–1 (CD11b/CD18) reduces intimal thickening after angioplasty or stent implantation in rabbits", *Proc. Natl. Acad. Sci. USA*, vol. 95, No. 17, pp. 10134–10139 (Aug. 18, 1998).

Schwartz, R.S. et al., "Restenosis and the Proportional Neointimal Response to Coronary Artery Injury: Results in a Procine Model", *J. Am. Coll. Cardiol.*, vol. 19, No. 2, pp. 267–274 (Jan. 1992).

Schwartz, R. S. et al., "Restenosis After Balloon Agioplasty. A Practical Proliferative Model in Porcine Coronary Arteries", *Circulation*, vol. 82, No. 6, pp. 2190–2200 (Dec. 1990).

Serruys, P. et al., "Heparin–Coated Palmaz–Schatz Stents in Human Coronary Arteries. Early Outcome of the Benestent–II Pilot Study", *Circulation*, vol. 93, No. 3, pp. 412–422 (Feb. 1, 1996).

Shih, C.C. et al., "The cytotoxicity of corrosion products of ntinol stent wire on cultured smooth muscle cells", *J. Biomed. Materials Research*, vol. 52, Issue 2, pp. 395–403 (Nov. 2000).

Simon, C. et al., "Protein Interactions with Endovasculr Prosthetic Surfaces", *J. of Long–Term Effects of Medical Implants*, vol. 10, Issue 1&2, pp. 127–141 (2000).

Sprague, E.A. et al., "Electrostatic Forces on the Surface of Metals as Measured by Atomic Force Microscopy", *J. of Long–Term Effects of Medical Implants*, vol. 10, Issue 1&2, pp. 111–125 (2000).

Sukhova, G.K. et al., "Expression of the Elastolytic cathepsins S and K in Human Atheroma and Regulation of their Production in Smooth Muscle Cells", *J. Clin. Invest.*, vol. 102, No. 3, pp. 576–583 (Aug. 1, 1998).

Torgersen, S. et al., "Immunocompetent Cells Adjacent to Stainless Stell and Titanium Miniplates and Screws", *Eur. J. Oral Sci.*, vol. 103, No. 1, pp. 46–54 (Feb. 1995).

Whelan, D.M. et al., "Foreign Body Contamination During Stent Implantation", *Cathet. and Cardiovas. Diagnosis*, vol. 40, pp. 328–332 (1997).

Willerson, J.T., "Stent Restenosis. Can Effective Antithrombotic Therapy Be Protective?", *Circulation*, vol. 96, No. 2, pp. 383–385 (Jul. 15, 1997).

Winter, G.D., "Tissue Reactions to Metallic Wear and Corrosion Products in Human Patients", *J. Biomed. Mater. Res. Symposium*, No. 5, Part 1, pp. 11–26 (1974).

Yutani, C. et al., "Histologic Evidence of Foreign Body Granulation Tissue and de novo Lesions in Patients with Coronary Stent Restenosis", *Cardiology*, vol. 92, No. 3, pp.171–177 (1999).

\* cited by examiner

FIG. 4
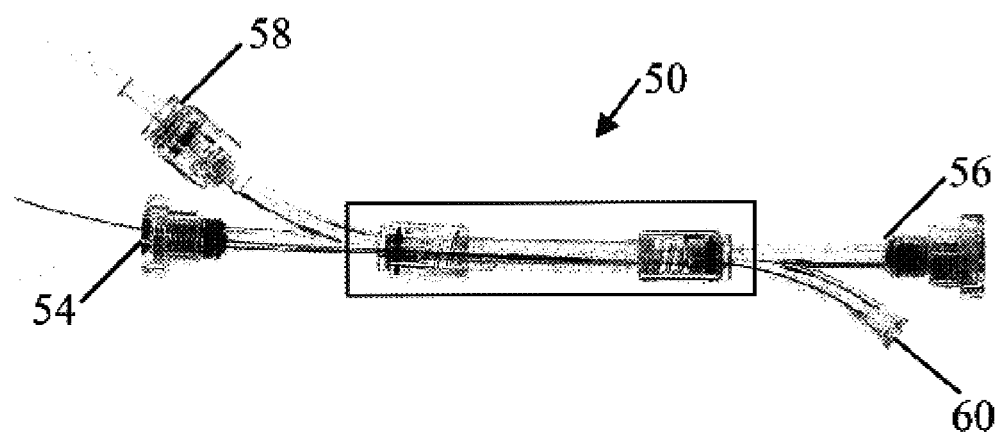
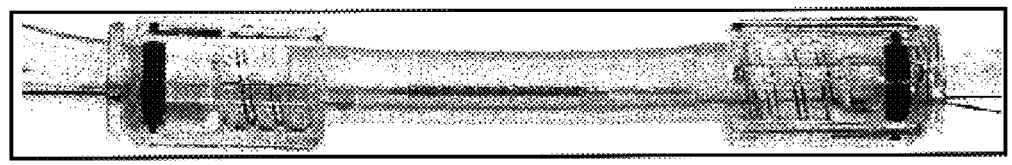

STENT TREATMENT APPARATUS AND METHOD

TECHNICAL FIELD

The invention relates generally to the field of angioplasty and more specifically to stent implantation after angioplasty. More specifically, the invention relates to methods and means of reducing coronary restenosis.

BACKGROUND

Coronary restenosis after angioplasty and stent implantation placement remains a substantial problem, as outlined by Willerson, J. T., 1997, *Circulation*, 96:383–385. While recent randomized studies show that stent implantation reduces restenosis significantly compared to balloon angioplasty (see Rankin, J. M., et al., 1999, *N Engl J Med*, 341:2005–6), stents have not eliminated restenosis, especially in complex lesion subsets such as diffuse disease and small vessels. The observation that in-stent restenosis may be diffuse suggests that a generalized reaction to the stent may be a possible etiology. Such a reaction might be to the metal, or alternatively from residual contaminants on the stent from the manufacturing process, as described by Shih, C. C. et al., 2000, *J Biomed Mater Res*, 52:395–403.

Previous animal studies established a significant correlation between the degree of arterial injury caused by metallic wire coils and the resultant neointimal thickness and lumen stenosis at the stent site. See Schwartz, R. S. et al., 1992, *J Am Coll Cadiol*, 19:267–74, and Karas, S. P. et al., 1992, *J Am Coll Cardiol*, 20:467–74.

More recently, the inflammatory reaction induced by stent struts after stent manipulation was found positively associated with neointimal hyperplasia. See Kornowski, R. et al., 1998, *J Am Coll Cardiol*, 31:224–30. Chronic inflammatory cells around stent struts have also been seen in a recent pathology report of coronary stenting in humans (Farb, A. et al., 1992, *Circulation*, 99:44–52).

In light of these findings, a reduction of the stent-induced inflammatory response has the potential to prevent excessive neointimal formation within stents. Measures directed at inhibiting adhesion molecules (Barron, M. K. et al., 1997, *Circulation*, 96:3587–3592), tissue proteinases (Lucas, A. et al., 1996, *Circulation*, 94:2890–900) and macrophage activation (Rogers, C. et al., 1998, *Proc. Natl. Acad. Sci. USA*, 95:10134–10139) have been tested to suppress the inflammatory reaction after vascular injury, but further experimentation is required to better understand their clinical relevance.

Several reports indicate that manual stent manipulation before implantation may cause foreign body contamination (Whelan, D. M. et al., 1997, *Cathet Cardiovasc Diagn*, 40:328–332; Kornowski, R. et al., 1999, *Coronary Artery Dis*, 10:9–14) and increased neointimal hyperplasia (Kornowski, R., et al., 1998, *J Am Coll Cardiol*, 31:224–30).

Restenosis remains an important limitation of percutaneous interventions for coronary artery disease, despite major procedural advances over the past decade. Experimental studies and pathology reports suggest important relationships among inflammation, vascular injury, and neointimal growth. Monocytes contribute to neointimal thickening with bulk within the intima (see Moreno, P. R., et al., 1996, *Circulation*, 94:3098–3102) by generating injurious reactive oxygen intermediates, as noted by Peri, G. et al, 1990, *J. Immunol*, 144:1444–1448, and through elaboration of growth and chemotactic factors (see Assoian, et al., 1987, *Proc. Natl. Acad. Sci. USA*, 84:6020–6024), as well as by matrix metalloproteinase production capable of degrading extracellular constituents, thereby facilitating cell migration (Sukhova, G. K., et al., 1998, *J. Clin. Invest*, 102:576–583).

SUMMARY

We have determined that exposing sterile stents to a high pressure wash immediately before implantation can eliminate residual surface stent contaminants and reduce the inflammatory response elicited by the stent.

Accordingly, the invention is found in a stent treatment apparatus that includes a stent washing chamber that is configured to accept a stent, a fluid inflow port, and a fluid outflow port. The fluid inflow port and the fluid outflow port are in fluid communication with the stent washing chamber.

The invention is also found in a stent treatment apparatus that includes stent washing means for pressure washing a stent preloaded on a balloon catheter, as well as fluid inflow means for providing a washing fluid to the stent washing means and fluid outflow means for removing the washing fluid from the stent washing means. The apparatus also includes receiving means for receiving a catheter within the stent washing apparatus.

The invention is also found in a stent delivery system that includes a stent and a stent washing apparatus, where the apparatus includes a stent washing chamber that has an inlet, an outlet, and a central region configured to accept a stent. The apparatus also has a fluid inflow port and a fluid outflow port, with the fluid inflow port and the fluid outflow port in fluid communication with the stent washing chamber.

The invention is also found in a method of delivering a stent. The method includes steps of placing a preloaded stent into a stent washing apparatus, contacting the preloaded stent with a washing fluid under pressure, removing the washing fluid, and extending the preloaded stent beyond the stent washing apparatus into a touhy.

The invention is also found in a method of loading a stent with a drug. The method includes steps of placing a preloaded stent into a stent washing apparatus, contacting the preloaded stent with a solution comprising a drug, providing sufficient residence time to permit transfer of the drug into and onto the stent, removing the drug solution, and extending the preloaded stent beyond the stent washing apparatus into a touhy.

BRIEF DESCRIPTION OF THE FIGURES

FIG. 4 represents a stent-cleaning chamber as used in the working examples described hereinafter.

FIG. 6A shows regression lines for handled and handled+rinsed stents, while FIG. 6B shows injury-dependent neointimal thickness regression lines for untouched and untouched+rinsed stents.

In FIG. 7A, the thicker neointima in the handled stent artery overlies the struts that elicited more inflammation (in asterisks) while in FIG. 7B, handled+rinsed struts elicited minimal neointima even with severe medial damage (arrows).

FIG. 9A provides representative linear fit curves of injury-dependent inflammation in the four studied groups while

DETAILED DESCRIPTION OF PREFERRED EMBODIMENTS

The present invention is directed to methods, means and apparatuses for washing stents prior to implantation. In a preferred embodiment, this washing procedure results in a stent that bears fewer foreign contaminants and thus causes a reduced level of inflammation once the stent is implanted.

A stent is frequently used as part of a balloon angioplasty procedure. This procedure is often-times referred to as a percutaneous transluminal coronary angioplasty (PTCA) procedure. Typically, an angioplasty procedure is called for when one or more of the arteries providing blood to the heart are partially or completely obstructed. In brief, a small balloon is placed within the constriction in the artery and is inflated, thereby forcing the constriction to open up.

Angioplasty typically begins by making a needle puncture in the femoral artery, which is located in the patient's groin. A short tube called a sheath is placed through the needle puncture and extends into the femoral artery. The sheath can function as an access port for the catheters used to open the blockages or constrictions present in the cardiac arteries.

Once the sheath has been placed, a guide catheter is inserted into the sheath and follows the femoral artery to the aorta, through the aorta and into position within the subject artery. Contrast dyes can be used so that the physician can visualize the obstructions.

Next, a guide wire is placed within the guide catheter and preferably is inserted such that it extends through and beyond the particular blockage of interest. The guide wire can function as a track for the balloon catheter that follows. The balloon catheter is fed along the guide wire until the un-inflated balloon is in position within the blockage. The balloon is slowly inflated, which is intended to remove the constriction within the artery. Afterwards, the balloon is deflated and contrast dye is again injected into the artery to see if the interior volume of the artery has been increased. Typically, it can take several balloon inflations to adequately expand the artery and to compress the deposits that were constricting the artery.

Frequently, a stent is placed within the previously blocked area to help prevent restenosis, which refers to the artery re-narrowing itself after the angioplasty procedure. Once the balloon catheter has been removed, another balloon catheter that bears a compressed, preloaded stent can be advanced along the guide wire until the stent is in position within the previously blocked area. The balloon is inflated, which expands and positions the stent.

Figure 3:
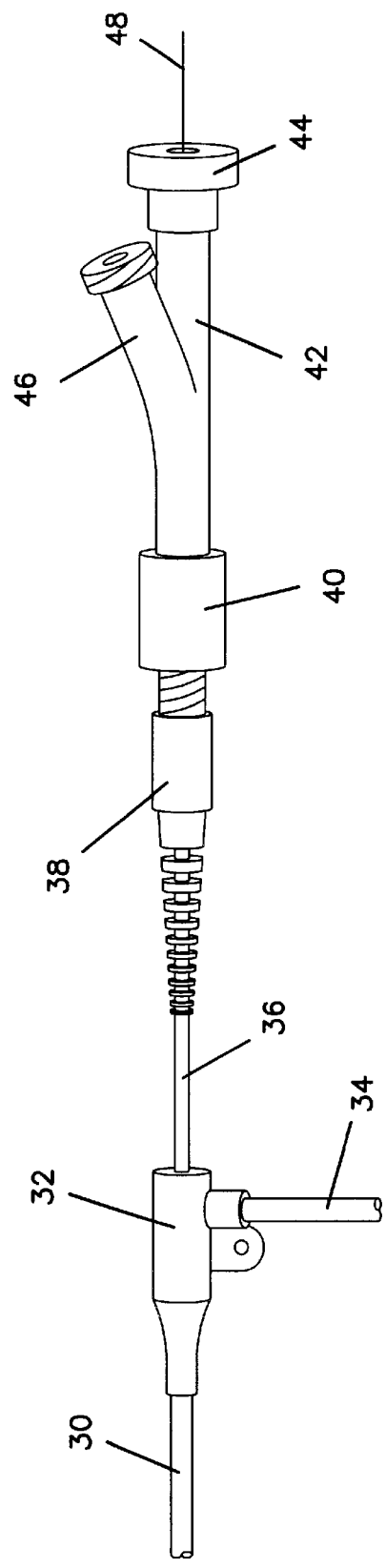
FIG. 3 is a diagrammatical view of a sheath, a guide catheter and a touhy, to which a stent treatment apparatus can be attached in accordance with a preferred embodiment of the present invention.

FIG. 3 is a schematic illustration of the equipment used to place a stent within an artery. One end of the sheath 30 is placed within a needle puncture made in the femoral artery, as described above. A second end of the sheath 30 extends beyond the patient's skin and includes a coupling 32. The coupling 32 includes a side arm 34 that can be used for a variety of different purposes, although injecting dye is probably the most common use for the side arm 34.

The coupling 32 is configured to accept a guide catheter 36 which in turn has at one end a coupling 38. In a preferred embodiment, the coupling 38 is the male portion of a luer lock that interacts with the coupling 40 that is present at one end of the touhy 42. Again, in a preferred embodiment, the coupling 40 is the female portion of a luer lock. For illustrative purposes, the guide catheter 36 is illustrated as fully or nearly fully inserted into the sheath 30. Typically, the guide catheter 36 does not penetrate this far.

The touhy 42 is a Y-shaped apparatus that has a contrast port 46 that is typically used for injecting dye, as well as a linear portion having at one end a coupling 44. Preferably, the coupling 44 is a hemostatic valve that includes reversible means to prevent blood from backing up through the guide catheter and out into the environment of the cardiac catheter lab, where these procedures are typically carried out. A guide wire 48, preferably left in place from a preceding angioplasty procedure, extends from the proximal end of the touhy 42.

Figure 1:
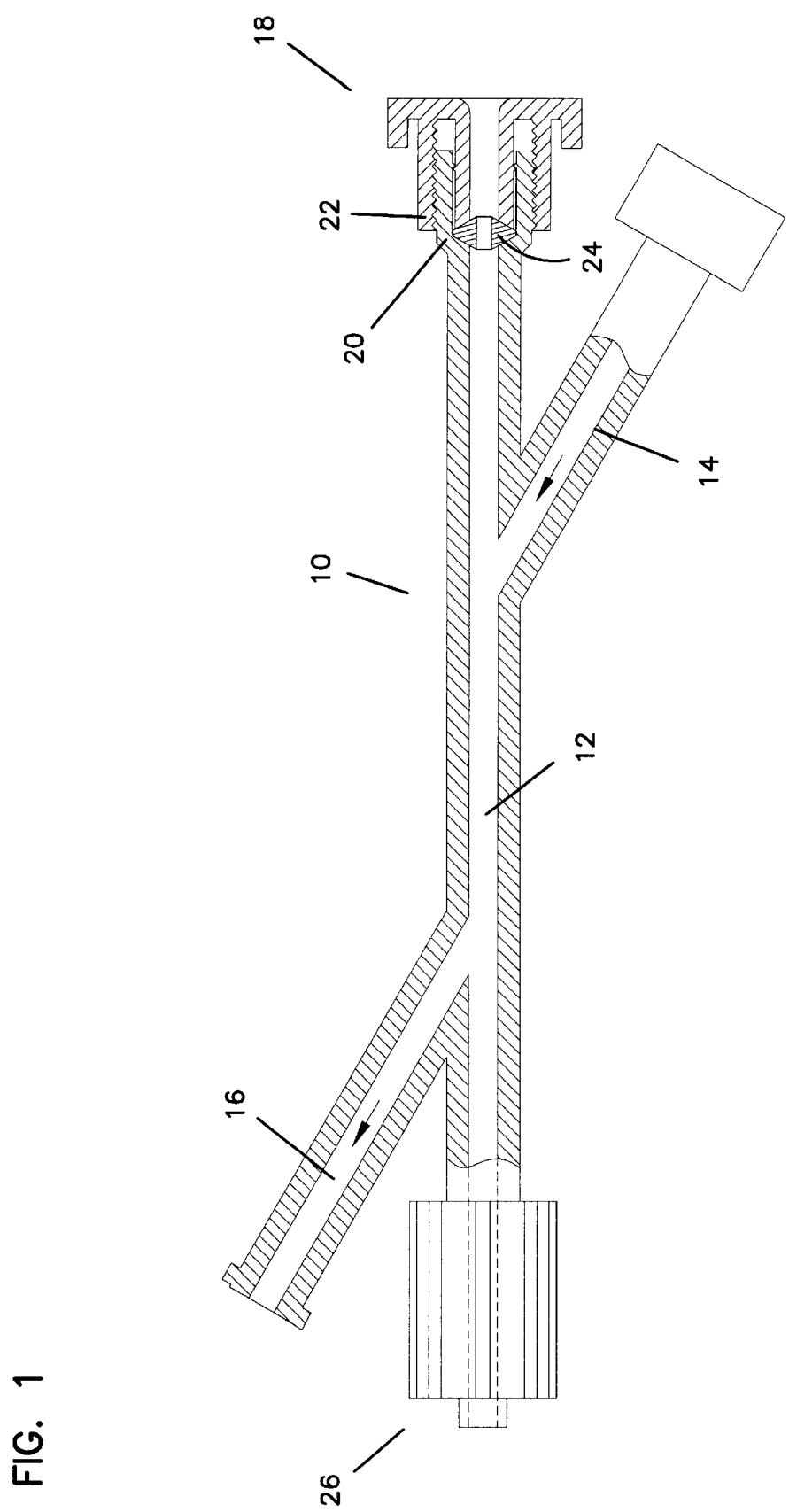
FIG. 1 is a cross-sectional view of a stent treatment apparatus in accordance with a preferred embodiment of the present invention.

The present invention is directed to a stent treatment apparatus 10 that can be connected to the proximal end of the touhy 42. In an alternate embodiment, the stent treatment apparatus 10 can indeed substitute for the touhy 42 and therefore can connect directly to the coupling 38 located at the proximal end of the guide catheter 36. FIG. 1 illustrates a preferred embodiment of the stent treatment apparatus 10 that has a stent washing chamber 12 that is fluidly connected to an inlet port 14 and an outlet port 16.

The stent treatment apparatus 10 has a first end 18 through which a balloon catheter bearing a preloaded stent can be inserted. Preferably, the first end 18 includes a hemostatic valve that be reversibly closed to fluid flow. The valve includes an outer portion 22 that is threadedly engaged with a threaded portion 20 of the stent treatment apparatus 10. As the outer portion 22 is threaded farther onto the threaded portion 20, the compression washer 24 is compressed, thereby closing the valve to fluid flow.

The stent treatment apparatus 10 has a second end 26 that is configured to engage with the proximal end of a touhy 42 (see FIG. 3). Preferably, the second end 26 is configured to reversibly prevent fluid from flowing through the second end 26. In a preferred embodiment, the second end 26 can include a hemostatic valve. In another embodiment, the second end 26 can include a threaded cap (not seen) that can be used to prevent fluid flow when not desired.

Figure 2:
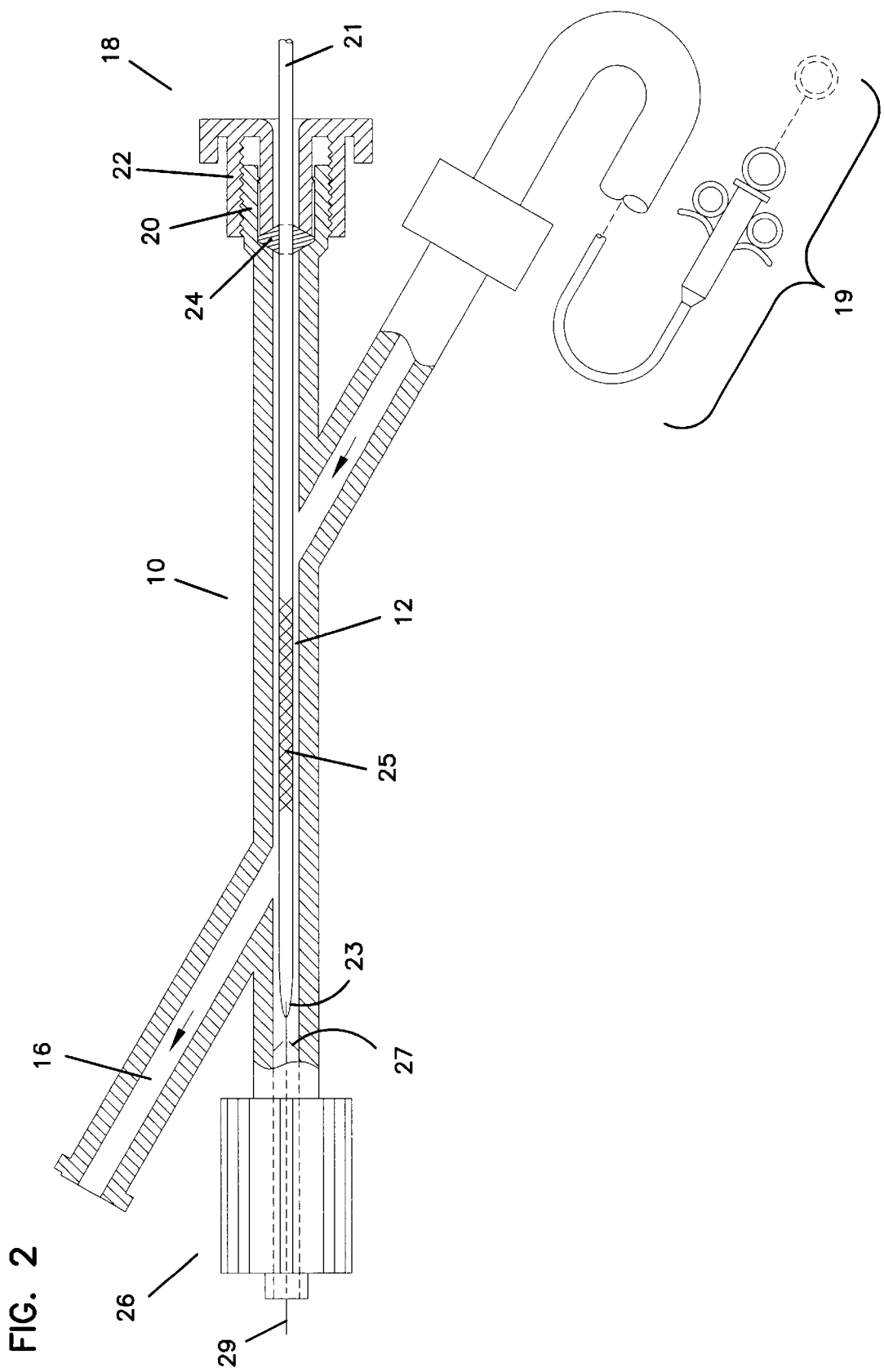
FIG. 2 is a cross-sectional view of a stent treatment apparatus in accordance with a preferred embodiment of the present invention, illustrating the relative placement of a balloon catheter bearing a preloaded stent and a guide wire. An inflation device for providing a treatment or wash fluid under pressure is also illustrated.

FIG. 2 illustrates a preferred embodiment of the stent treatment apparatus 10 in which the inlet port 14 includes a pressurized source 19 of a treatment fluid. The treatment fluid can be a wash fluid such as water and heparin, or can be a drug with which it is desired to coat a stent. In a preferred embodiment, the drug can be present as part of a polymeric mixture that will form a coating on the stent. The pressurized treatment fluid can also be air, if drying is desired. As illustrated, the pressurized source 19 is a syringe, although an indeflator can also be utilized.

As seen in FIG. 2, a guide wire 29 is in place within the stent washing chamber 12. A balloon catheter 21, bearing a preloaded stent 25, is placed over the guide wire 29 and is advanced into the stent washing chamber 12. In this particular embodiment, the stent washing chamber 12 includes a funnel structure 27 that helps direct the guide wire into and through the balloon catheter 21.

As discussed previously, the stent treatment apparatus 10 can be attached to a touhy 42, or can itself function as a touhy 42. The stent treatment apparatus 10 can be used to treat a stent 25 with a treatment fluid while the apparatus 10 is either connected to the touhy 42 or is itself functioning as the touhy. However, it is preferred that the stent treatment apparatus 10, with a stent 25 inside, is used prior to connecting to a touhy. In a preferred embodiment, the stent treatment apparatus 10 can be snapped off or otherwise removed from the touhy 42 once the stent-laden balloon catheter 21 is extended into the guide catheter 36.

In a preferred use of the stent treatment apparatus 10, a balloon catheter 21 bearing a preloaded stent 25 is positioned within the stent washing chamber 12, as illustrated for example in FIG. 2. Alternatively, as is often the practice in Europe, the stent can be hand-crimped onto the balloon catheter 21. In either case, the stent 25 is positioned within the stent washing chamber 12 and the first and second ends 18 and 26, respectively, of the stent treatment apparatus 10 are closed to fluid flow.

Next, a treatment fluid under pressure is injected into the inlet port 14, where the fluid flows past the stent 25 and exits through the outlet port 16. Preferably, the treatment fluid is a wash fluid that includes a water-heparin mixture. In a preferred embodiment, the wash fluid flows in laminar fashion past the stent, as this has been found to be optimal due to the charge differences between the plastic balloon and the stainless steel or nitinol stent. Morover, while neutral wash fluids can be employed, it is preferable to use a positively charged fluid as this interacts more effectively with the negatively charged metal ions found in and on the stent as a result of the manufacturing process.

Once the stent 25 has been washed, thereby reducing the level of foreign contamination, the inflow port 14 and the outflow port 16 are closed to fluid flow and the second end 26 of the stent treatment apparatus 10 can be attached to the proximal end of the touhy 42.

The following non-limiting examples are intended merely to illustrate the present invention.

WORKING EXAMPLE 1

FIG. 4 illustrates an embodiment of a stent cleaning chamber 50 as utilized in the working examples described herein. The stent cleaning chamber 50 was made using silicone rubber tubing 52 connected between two hemostatic valves 54 and 56. The stent cleaning chamber was sterilized before use via ethylene oxide sterilization. Pre-mounted stents were advanced through the hemostatic valve and were locked in the chamber closing the proximal valve 54 and the distal valve 56. An inflow port 58 allowed connection to an indeflator containing the rinsing solution, and an outflow port 60 permitted drainage of the solution and stent contaminants.

A solution of 40 ml of sterile ultrapure water (Barmstead, Dubuque, Iowa) with 25 U/ml of heparin (Elkins-Sinn, Inc. Cherry Hill, N.J.) was injected through the stent cleaning chamber at a sustained pressure of 4 atm (about 405 kPa) for a duration of 10 seconds, at a flow rate of 4 ml/second. After the process was complete the output port was closed, the distal valve was opened, and the stent was advanced to the desired coronary artery.

In this working example, several distinct levels of stent manipulation were tested, as indicated:

Untouched Stents

These stents were implanted without manipulation. The time elapsed between opening of the sterile package and stent implantation was less than 30 seconds, and neither stent nor balloon were touched by the operator.

Handled Stents

These stents were manually re-crimped on the balloon within 10 seconds of implantation. Sterile gloves directly from their commercial package were used for stent crimping. Stents were allowed to sit on a sterile table for not more than 3 minutes before implantation.

Rinsed Stents

These stents were pressure-rinsed with sterile heparinized ultrapure water in the stent cleaning chamber illustrated in FIG. 4 immediately before implantation.

Ex-vivo Surface Stent Analysis

The stent-cleaning chamber described above was first evaluated ex-vivo to assess reduction of surface foreign materials after stent pressure-rinsing. Six pre-mounted balloon-expandable 16 mm NIR stents (Boston Scientific Scimed, Inc., Maple Grove, Minn.) were expanded ex-vivo under sterile conditions as untouched (n=2), handled (n=2), and rinsed (n=2). After expansion, stents were collected in a sterile polypropylene tube for immediate ultrastructural evaluation by means of a Hitachi S-4700 scanning electron microscope. Digital scanning electron microscopy images of the stents were obtained and surface particles on the stents were counted by means of a digital imaging system (Sigmascan Pro 5.0, SPSS Inc., Chicago, Ill.) on three random samples of each stent at a 1:250 magnification.

Ex-vivo Evaluation of Stent Rinsing

Untouched stents had an average of 64±9.2 surface contaminant particles, while 164.7±10.3 contaminant particles were detected on handled stents, and 25.7±6.9 surface contaminants were found on rinsed stents. The number of contaminants on rinsed stents were significantly reduced compared to untouched stents (p=0.01) and handled stents (P<0.001). The contaminants were both outside and inside the stent surface, and in handled stents the foreign material was likely derived from gloves' powder.

Figure 5A:
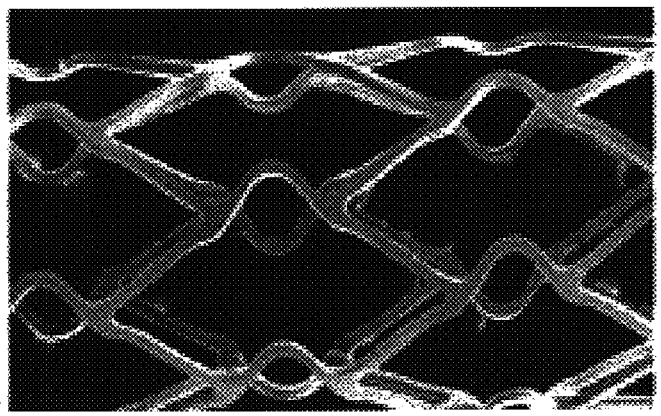
FIGS. 5A–5I provide an examination of the stent surface of six pre-mounted balloon-expandable 16-mm NIR stents that were expanded ex-vivo under sterile conditions as untouched, handled, and rinsed and evaluated by scanning electron microscope.
Figure 5B:
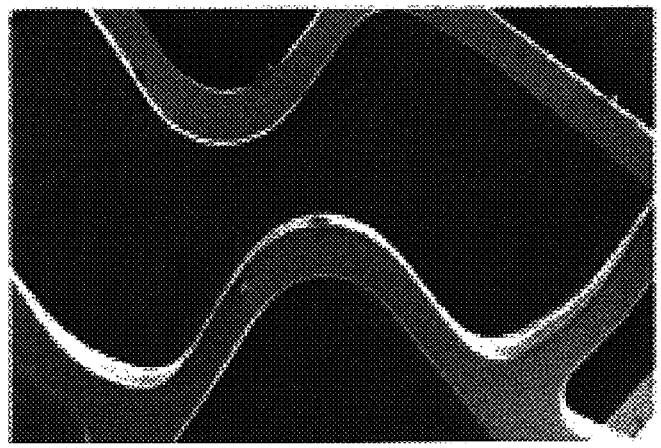
Figure 5C:
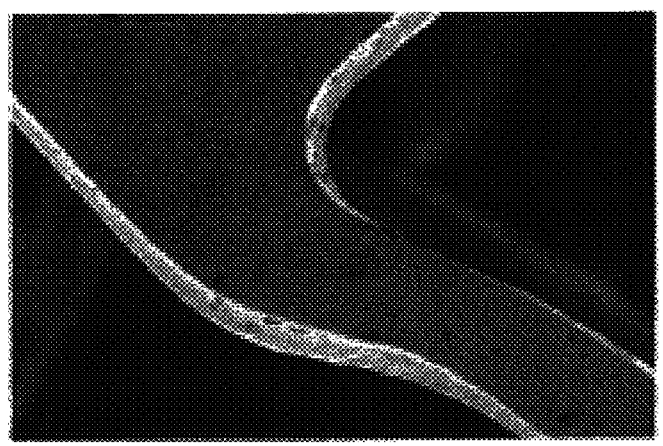
Figure 5D:
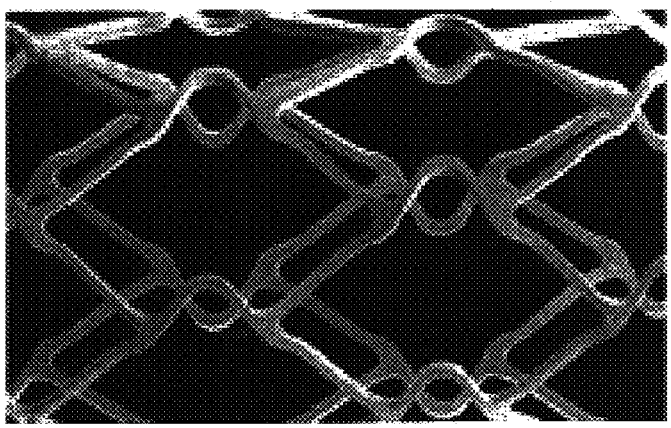
Figure 5E:
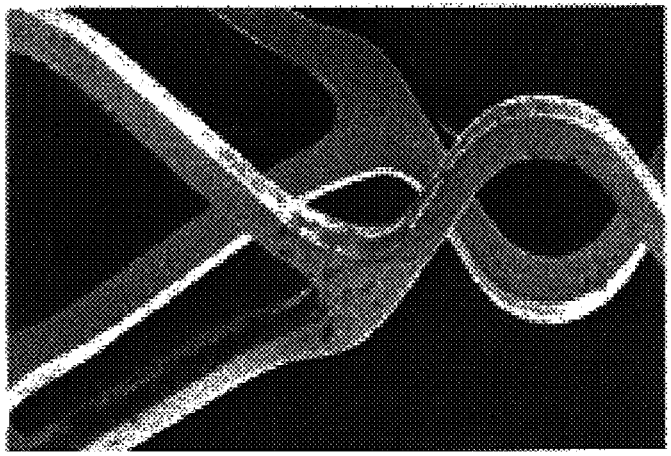
Figure 5F:
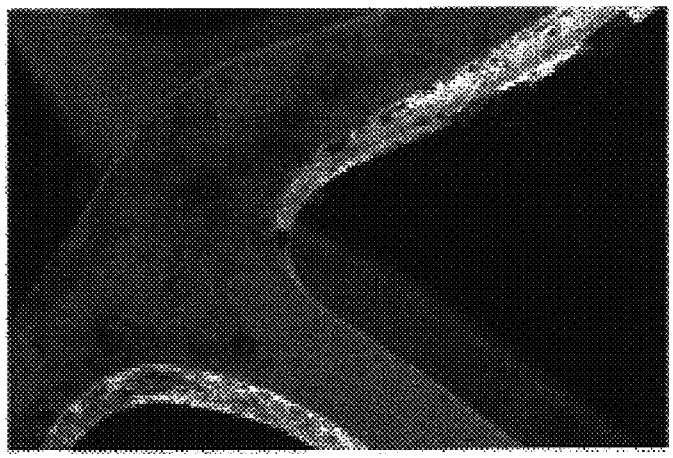
Figure 5G:
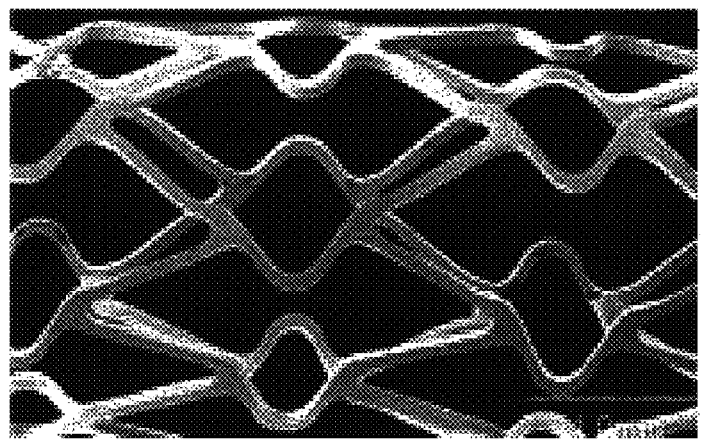
Figure 5H:
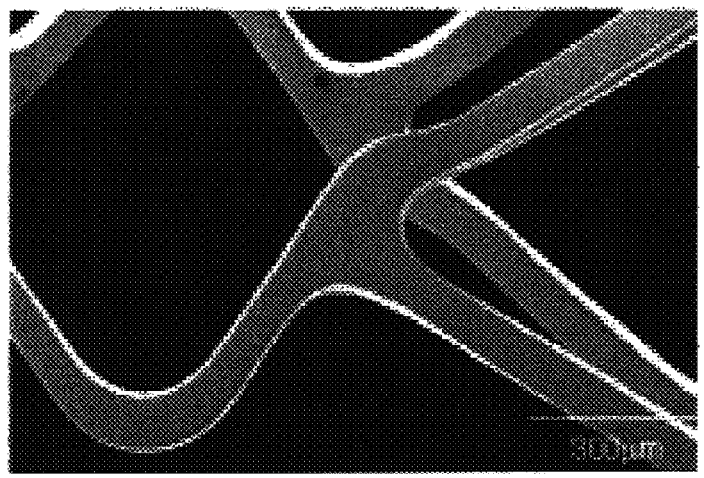
Figure 5I:
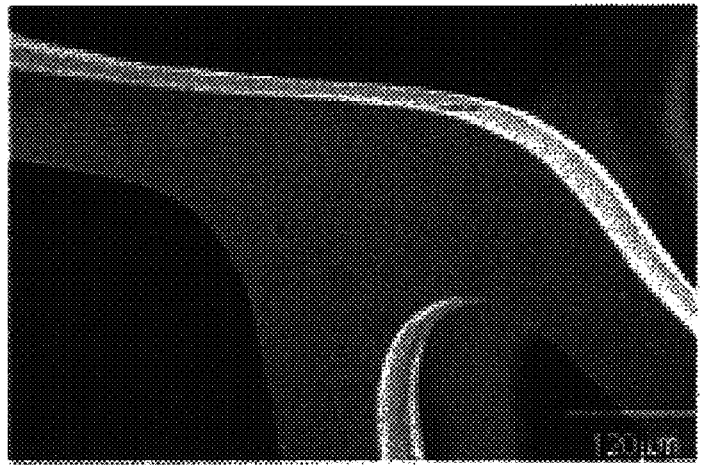

The results are seen visually in FIGS. 5A through 5I. FIGS. 5A, 5B and 5C are, respectively, microphotographs of an untouched stent taken at increasing magnification. FIGS. 5D, 5E and 5F are photographs of a handled stent, taken at the same magnification levels. It is apparent that the handled stents carry a higher level of foreign matter than the untouched stents. Finally, FIGS. 5G, 5H and 5I show a stent that has been rinsed as described above. The rinsed stent clearly carries a significantly reduced level of foreign contaminants.

The stent-cleaning chamber appears to improve removal of surface contaminants. Given the comparability of restenosis rates across clinically used stents, this finding likely suggest that other stents would show similar effects. Numerous studies suggest that foreign bodies activate macrophages (Winter, G. D., 1974, *J Biomed Mater Res*, 8:11–26; Rogers, C. et al., 1995, *Circulation*, 91:2995–3001). Corrosion products of metal implants (Torgesen, S. et al., 1995, *Eur J Oral Sci*, 103:46–54) and powdered biomaterials (Pizzoferrato, A. et al., 1987, *Biomed Mater Res*, 21:419–428) may elicit these reactions during stent implantation.

Our ex-vivo analysis showed a substantial number of surface foreign materials in untouched and especially in handled stents, likely derived from metal debris (possibly from laser cutting during stent manufacturing) or talc powder from operators' gloves. Similar results were reported in pre-mounted and hand-crimped stents using scanning electron microscopy with energy-dispersive elemental analysis (Jung, F. et al., 1999, *Eur Heart J*, 20:628). Pressure-rinsing of stents with the stent-cleaning chamber successfully removed most of the surface stent contaminants.

WORKING EXAMPLE 2

Animal Study Protocol

Animal studies were performed with the approval of the Institutional Animal Care and Use Committee of the Mayo Foundation. Eight domestic pigs (Sus scrofa; weight 29±3 kg) underwent oversized coronary stent implantation as described previously (Schwartz, R. S., et al., 1990, *Circulation*, 82:2190–200). Three days before the procedure, pigs began oral aspirin (325 mg) that was continued for the remainder of their course. General anesthesia was achieved with ketamine (3 mg/kg IM) and xylazine (30 mg/kg IM). Additional medication at the time of induction included atropine (1 mg IM) and an antibiotic (flocillin, 1 g IM). During the angioplasty procedure, an intraarterial bolus of heparin (10,000 U) was administered. Under sterile conditions, an 8F sheath was inserted into the left carotid artery, and a JL3.5 (Cordis) guide catheter was advanced to the ostium of the desired coronary artery under fluoroscopic guidance. Continuous hemodynamic monitoring and surface electrocardiographic monitoring was maintained throughout the procedure.

Four stents with different degrees of manipulation were randomly implanted in the LAD, proximal RCA, distal RCA, and LCX arteries in each animal. In one animal, coronary anatomy was suited for implantation of two stents in the LCX (proximal and distal), one in the LAD and one in the RCA. Pre-mounted balloon expandable 16 mm NIR stents (Boston Scientific Scimed, Inc., Maple Grove, Minn.) were deployed at 8 atm (about 810 kPa) for 30 seconds to achieve a stent/vessel ratio of 1.2:1.

Repeat angiograms were obtained after stent implantation. All equipment was removed and the carotid artery was ligated. All animals received 325 mg of aspirin and 75 mg of clopidogrel orally daily until euthanasia. Meticulous attention was undertaken during the procedure to avoid contamination of any transcatheter device. Four weeks later the animals were euthanized and the coronary arteries were perfusion-fixed for histologic analysis.

Histological Analysis

The hearts were fixed in 10% buffered formalin for 24 hours. The treated coronary segments were harvested, dehydrated in ascending alcohols and infiltrated with methylmethacrylate (MMA). Specimens were kept at 4° C. during dehydration and infiltration of the tissue. The MMA was a mixture of uninhibited methylmethacrylate, polyethylene glycol distearate, dibutylphthalate, and benzoyl peroxide. After polymerization (at room temperature in presence of nitrogen), 5 $\mu$m sections were cut using a heavy-duty rotary microtome (Leica RM 2165, Minneapolis, Minn.) with a D-profile tungsten-carbide knife. Modified van Gieson staining and hematoxylin-eosin staining were then performed using these free-floating sections.

Morphometric analysis of the neointima from histology slides included the degree of injury (injury score), inflammatory score, and morphometric analysis of neointimal area, neointimal thickness and percent of vessel stenosis. Histomorphometry was performed on elastin sections using a microscope coupled to a digital morphometry system (Diagnostic Instruments, Inc.). Measurements were made on three cross sections from each stent. Injury score was assessed as previously described by Schwartz et al., ibid:

0=no injury;

1=break in the internal elastic lamina;

2=perforation of the media; and

3=perforation of the external elastic lamina to the adventitia.

The average injury score for a segment was calculated by dividing the sum of injury scores by the total number of struts at the examined section.

The inflammation score for each individual strut was graded as described by Kornowski et al (ibid):

0=no inflammatory cells surrounding the strut;

1=light, noncircumferential lympho-monocytic infiltrate surrounding the strut;

2=localized, moderate to dense cellular aggregate surrounding the strut noncircumferentially;

3=circumferential dense lympho-monocytic cell infiltration of the strut.

The inflammatory score for each cross section was calculated in the same manner as for the injury score. Vessel percent stenosis was calculated as:

$$\frac{\text{stenotic lumen area}}{\text{original lumen area}} \times 100$$

Statistical Analysis

Data are presented as mean value±SEM. A sample size of 8 arteries per group was chosen to allow detection of a projected difference in neointimal thickness of 0.1 mm at a power of 0.8. The groups that were normally distributed were compared by analysis of variance, or student's t test when appropriate. The groups that failed the normality test were compared by means of the Kruskal-Wallis one-way analysis of variance on ranks and the Mann-Whitney rank sum test. Associations among groups were assessed by Spearman rank correlation coefficients. Regression modeling was used to account for injury and the injury-dependent neointimal response (McKenna, C. J. et al., 1998, *Circulation*, 97:2551–6).

In brief, three models were used to establish whether there were differences in intercepts or slopes across groups by use of the following equations. Note that the variable labeled Gp establish the rinsed stent groups. The two rinsed stent groups (untouched+rinsed and handled+rinsed) were analyzed separately with their non-rinsed counterparts (untouched and handled):

Testing for differing intercepts:

Neointima=Constant+Injury Score+Gp

Testing for differing slopes (allowing an arbitrary intercept):

Neointima=Constant+Injury Score+Gp+Gp×Injury Score

Testing for differing slopes (forcing a fixed intercept):

Neointima=Constant+Injury Score+Gp×Injury Score

Similar regression analyses were performed to account for injury and injury-dependent inflammation.

Eight animals underwent successful implantation of four stents with different levels of manipulation. All pigs survived until euthanasia at 28 days. Four groups were evaluated:

untouched stents (8 arteries);
untouched+rinsed stents (8 arteries);
handled stents (8 arteries); and
handled+rinsed stents (8 arteries).

Neointimal Response to Injury

Histologic study revealed neointimal formation and lumen stenosis of varying magnitude within all 32 examined stents. Tables 1A and 1B (shown below) show the histomorphometric measurements performed in the four studied groups. No statistically significant differences in vessel injury were observed among groups.

Handled stents had thicker neointima than handled+rinsed stents (p=0.03), which translated in more vessel percent stenosis (p=0.003) and a smaller vessel lumen (p<0.001) (Table 1A). The trivial stent handling performed in this study increased vessel percent stenosis by 35.9%, from a mean stenosis of 32.6% in handled stents to 20.9% in handled+rinsed stents. Moreover, stent handling increased vessel percent stenosis by 15.3% compared to untouched stents. Handled stents showed a significant association between arterial injury and neointimal thickness (r=0.75; p=0.03), but this association was not found in handled+rinsed stents (r=0.459; p=0.25).

Figure 6A:
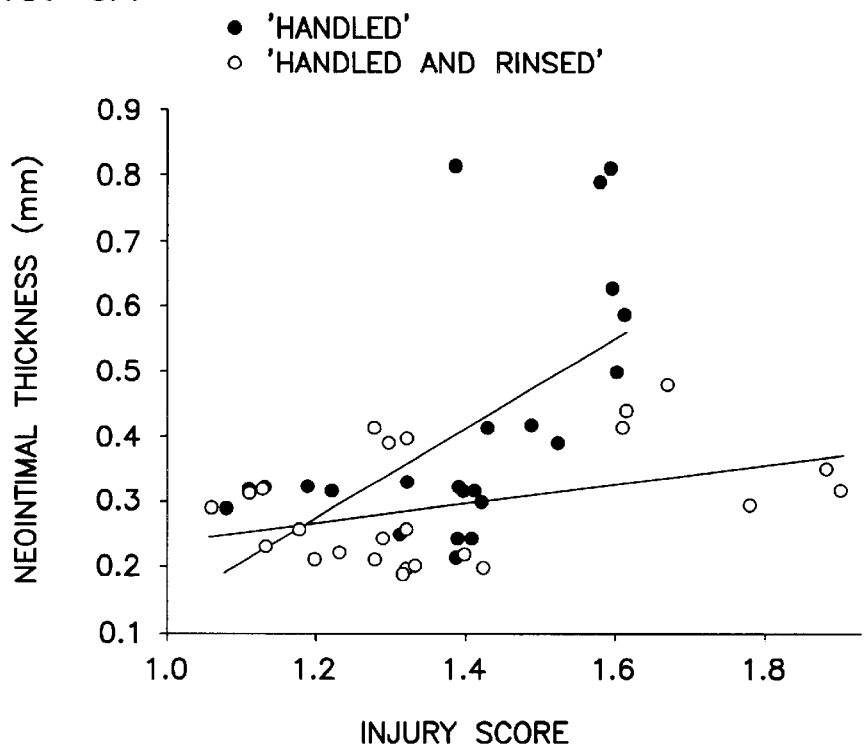
FIGS. 6A and 6B provide representative linear fit curves for injury-dependent neointimal thickness in the four studied groups.
Figure 6B:
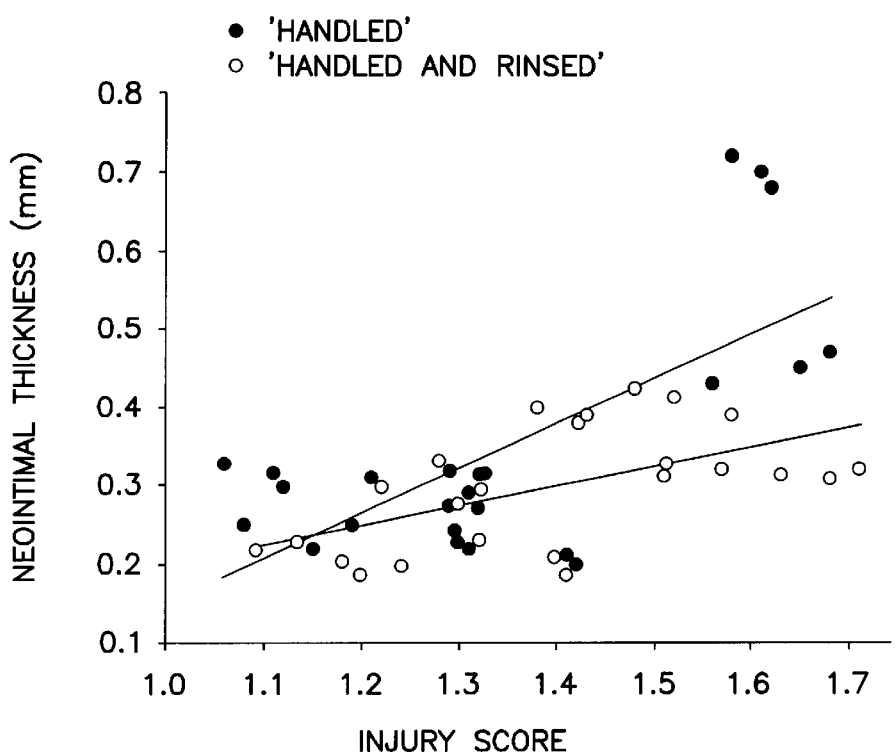
Figure 7A:
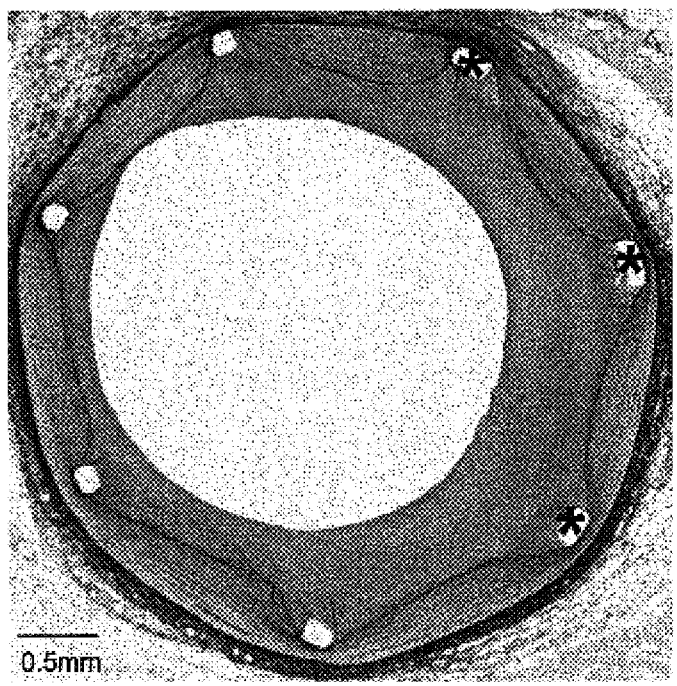
FIGS. 7A and 7B are histologic examples of handled and handled+rinsed stents. The two arteries have a similar mean injury score but a different neointimal response.
Figure 7B:
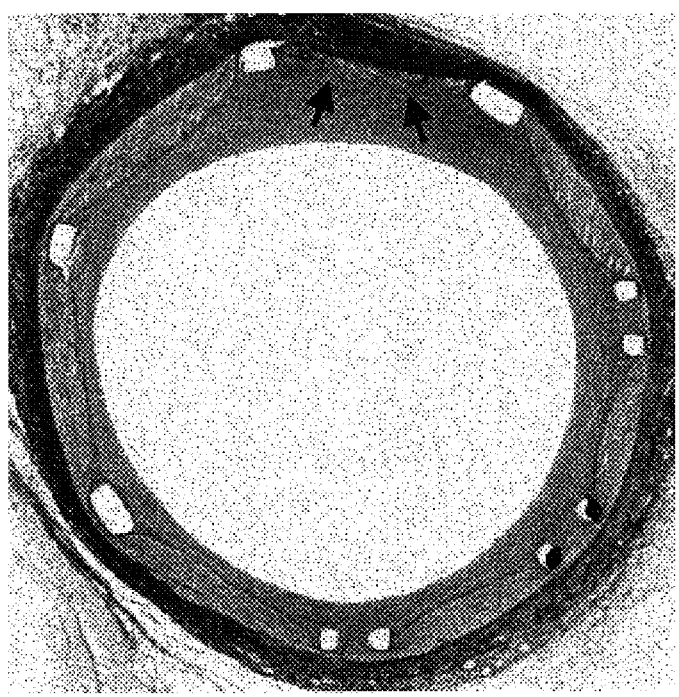

Representative linear fit curves for these correlations are presented in FIG. 6A. Regression analysis that accounted for injury and the injury-dependent neointimal thickness showed statistically significant differences in slopes, both allowing any intercept (p=0.004) or forcing a fixed intercept (p=0.003). No significant differences in intercepts were observed across groups (p=0.68)(FIG. 3A). FIGS. 7A and 7b are histologic examples of the neointimal response between handled and handled+rinsed stents with the same degree of arterial injury. The thicker neointima in the handled stent (FIG. 7A) overlies the struts that elicited a more intense inflammatory response (in asterisks).

No statistically significant differences in morphometric measurements were observed among untouched stents and untouched+rinsed stents (Table 1B). However, it is noteworthy that vessel percent stenosis was reduced by 17.4%, from a mean stenosis of 27.6% in untouched stents to 22.8% in untouched and rinsed stents. Untouched stents showed a significant association between the degree of arterial injury and neointimal thickness (r=0.72; p=0.04), and this association was again not found in untouched+rinsed stents (r=0.6;p=0.11). Representative linear fit curves for these correlations are presented in FIG. 7B. Regression analysis that accounted for injury and the injury-dependent neointimal thickness performed between untouched stents and untouched and rinsed stents showed statistically significant differences in slopes, both allowing any intercept (p=0.037) or forcing a fixed intercept (p=0.011). No significant differences in intercepts were observed across groups (p=0.06) (FIG. 7B).

Neointimal Response to Inflammation

Figure 8:
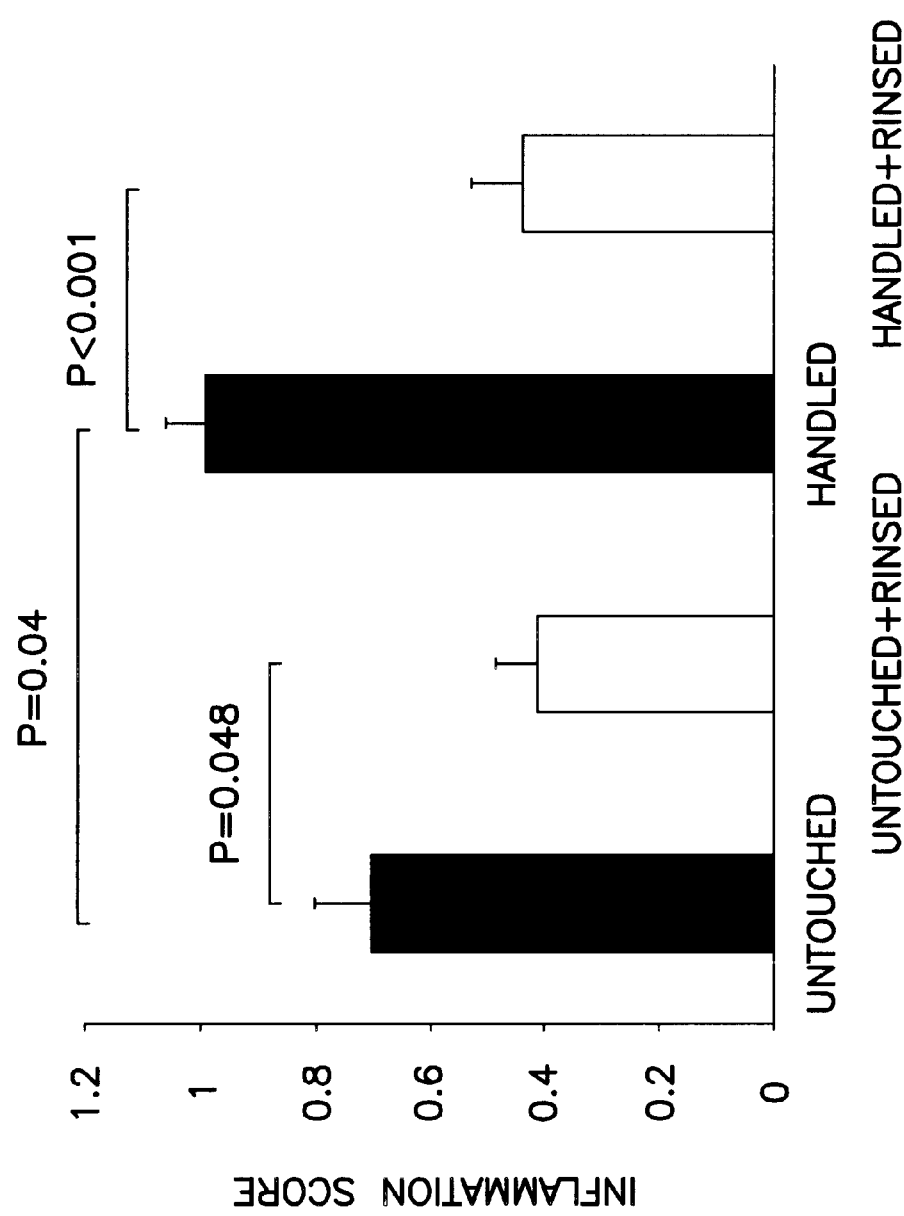
FIG. 8 provides inflammation scores for the four studied groups.

The absence of an association between arterial injury and neointimal thickness in both rinsed groups indicates that other factors, especially stent-induced inflammation, may play a determinant role in the development of neointimal hyperplasia after stent implantation. A mean inflammation score of 0.69±0.1 was found in untouched stents, 0.41±0.07 in untouched+rinsed stents, of 0.99±0.07 in handled stents, and 0.43±0.09 in handled+rinsed stents. A significant reduction in the inflammatory infiltrate around struts was observed in untouched+rinsed compared to untouched stents (p=0.048) and in handled+rinsed compared to handled stents (p<0.001). A difference was also observed between untouched and handled stents (p=0.04)(FIGS. 8A and 8B).

Table 2 summarizes the inflammation score of each strut in the four studied groups. 38 of 74 struts (51.4%) in untouched+rinsed and 51 of 77 struts (66.2%) in handled+rinsed stents had inflammatory scores of 0, and none had a score of 2.25 of 71 struts (35.2%) of untouched stents had an inflammatory score of 0. Only 6 of 73 struts (8.2%) of handled stents had a score of 0,59 struts (80.8%) had a score of 1, and 8 struts (10.9%) had a score of 2. No struts had an inflammation score of 3 in any group. These data suggest that commercially available untouched stents elicit a mild inflammatory response, which is further minimized after stent rinsing with high pressure.

The inflammatory reaction consisted of groups of mononuclear leukocytes adjacent to the struts. Small round lymphocytes and occasional polymorphonuclear leukocytes were also noted surrounding the struts. Fibrin microthrombi around the struts were also identified. In contrast, eosinophils and multinucleated foreign body giant cells were not observed, suggesting that no infection, allergy or excessive manipulation was caused to the handled stent struts.

Inflammatory Response to Injury

Figure 9A:
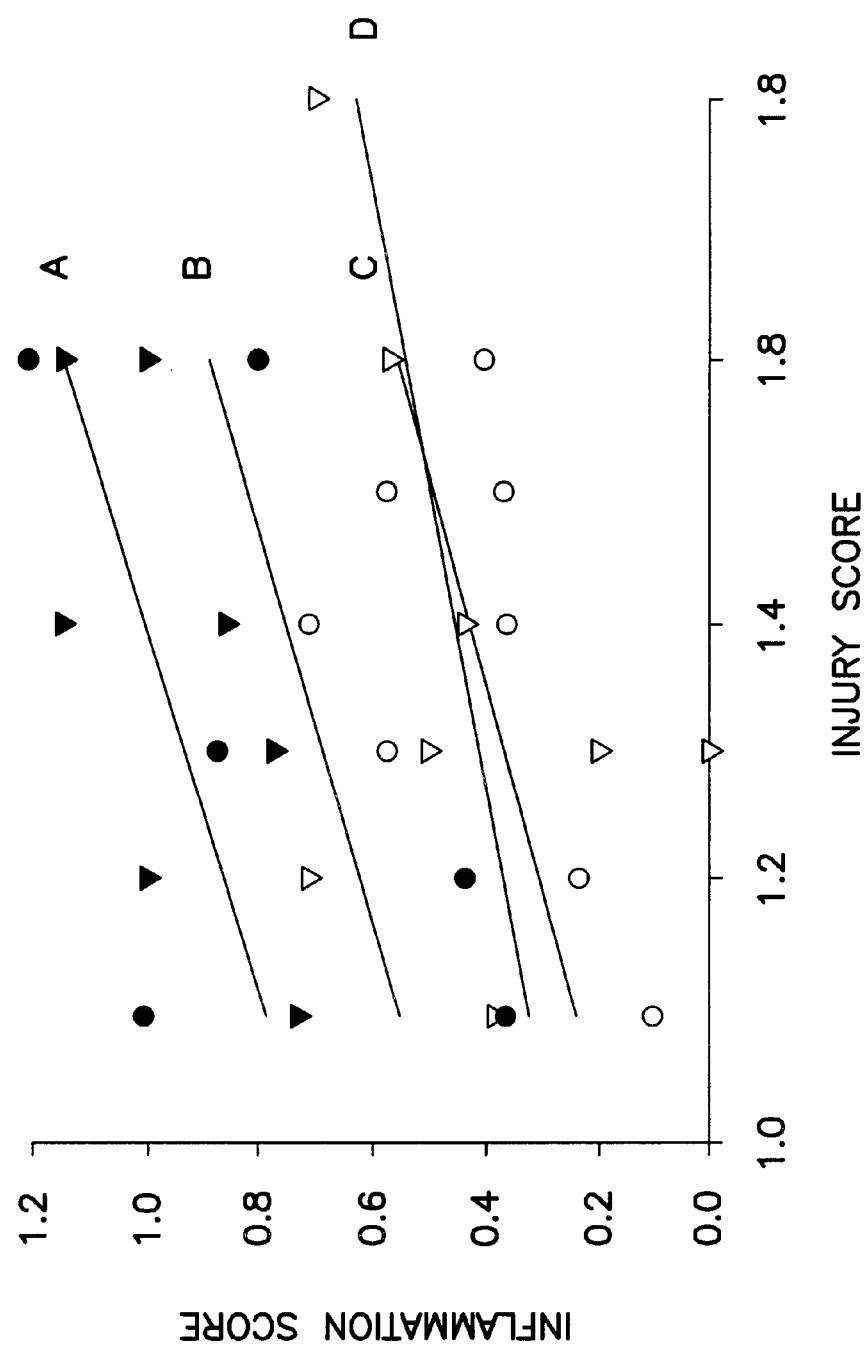
Figure 9B:
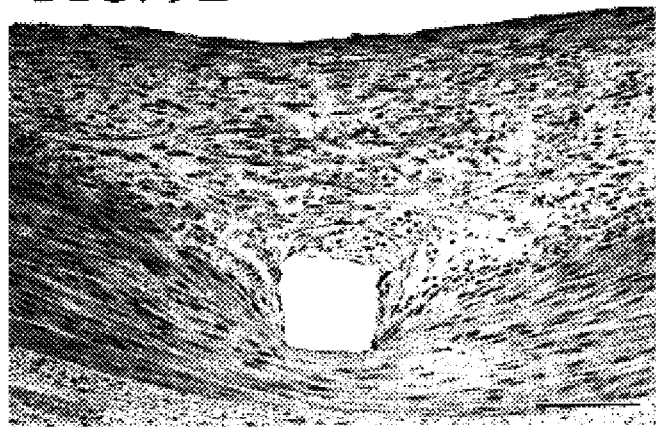
FIGS. 9B, 9C, and 9D are hematoxylin-eosin microphotographs of peri-strut inflammation.
Figure 9C:
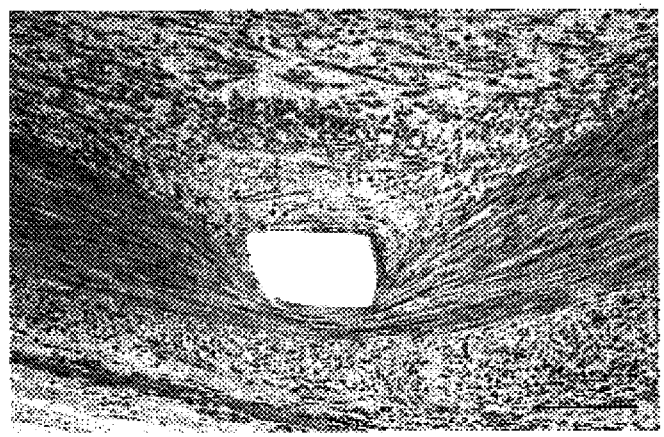
Figure 9D:
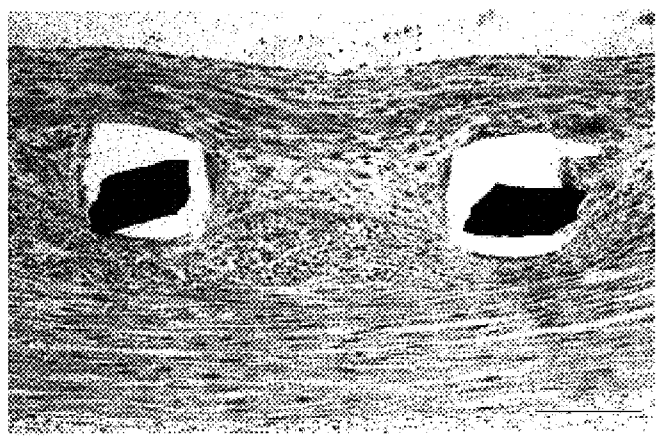

Regression analysis performed between injury and injury-dependent inflammation showed a significant difference in intercepts assuming equal slopes (p=0.008) and a significant difference in slopes assuming a fixed intercept (p<0.0001) between handled stents and handled+rinsed stents. We did not find significant differences in slopes assuming arbitrary intercepts across groups (p=0.47). Regression analysis comparing injury-dependent inflammation between untouched stents and untouched+rinsed stents showed a significant difference in intercepts assuming equal slopes (p=0.08) and a significant difference in slopes assuming a fixed intercept (p=0.01). Again, no significant differences in slopes assuming arbitrary intercepts were found across groups (p=0.78). Representative linear fit curves for these associations are presented in FIG. 9A. These data suggest that stent rinsing immediately before implantation reduces the inflammatory reaction surrounding stent struts, and that stent handling prior to implantation increases the inflammatory reaction around stent struts irrespective of the extent of injury. FIGS. 9B, C, and D are histologic examples of the inflammatory response observed around stent struts in untouched stents, handled stents, and handled+rinsed stents.

TABLE 1A

Histomorphometric measurements obtained from handled stents

| | Handled<br>n = 8 | Handled + rinsed<br>n = 8 | p |
|---|---|---|---|
| Injury Score | 1.38 ± 0.03 | 1.37 ± 0.05 | 0.33 |
| Lumen, mm$^2$ | 4.45 ± 0.2 | 7.0 ± 0.3 | <0.001 |
| Vessel Stenosis, % | 32.6 ± 3.2 | 20.9 ± 1.8 | 0.003 |
| Neointimal Thickness, mm | 0.39 ± 0.04 | 0.29 ± 0.02 | 0.03 |
| Neointimal Area, mm | 2.2 ± 0.2 | 1.7 ± 0.1 | 0.3 |

TABLE 1B

Histomorphometric measurements obtained from untouched stents.

| | Untouched<br>n = 8 | Untouched + rinsed<br>n = 8 | p |
|---|---|---|---|
| Injury Score | 1.34 ± 0.04 | 1.38 ± 0.04 | 0.35 |
| Lumen, mm$^2$ | 5.8 ± 0.4 | 5.4 ± 0.2 | 0.19 |
| Vessel Stenosis, % | 27.6 ± 3.1 | 22.8 ± 1.7 | 0.7 |

TABLE 1B-continued

Histomorphometric measurements obtained from untouched stents.

|  | Untouched n = 8 | Untouched + rinsed n = 8 | p |
|---|---|---|---|
| Neointimal Thickness, mm | 0.34 ± 0.03 | 0.29 ± 0.01 | 0.7 |
| Neointimal Area, mm | 1.9 ± 0.1 | 1.5 ± 0.1 | 0.04 |

TABLE 2

Inflammation score, ranging from 0 to 3, of each individual stent strut in the four studied groups.

|  | Untouched N = 71 | Untouched + rinsed N = 74 | Handled N = 73 | Handled + rinsed N = 77 |
|---|---|---|---|---|
| 0, n (%) | 25 (35.2) | 38 (51.4) | 6 (8.2) | 51 (66.2) |
| 1, n (%) | 42 (59.2) | 36 (48.6) | 59 (80.8) | 26 (33.8) |
| 2, n (%) | 4 (5.6) | 0 (0) | 8 (10.9) | 0 (0) |
| 3, n (%) | 0 (0) | 0 (0) | 0 (0) | 0 (0) |

N = total number of struts evaluated in each group.

It appears that stent rinsing modifies surface stent electrostatic forces. Yutani et al suggested that chronic inflammation stimulated by ion-coating materials around stent struts might give rise to smooth muscle cell proliferation and growth factor production by platelets in the thrombi (Yutani, C. et al., 1999, *Cardiology*, 92:171–177). Electrostatic forces on the surface of metals, such as the stent, are critical in influencing blood interactions with those surfaces and the vascular wall (Sprague, E. A., et al., 2000, *J Long Term Eff Med Implants*, 10:111–25). Simon et al studied the electrostatic forces residing on the surface of metal intravascular prostheses and found that protein binding was relatively uniform for all metallic surfaces including stainless steel 316L (Simon, C. et al., 2000, *J Long Term Eff Med Implants*, 10:127–41). In this study, metals were rinsed with PBS and post-elution determinations showed that proteins eluted from metallic surfaces, being albumin more easily eluted than fibrinogen and fibronectin. In light of these findings, it is reasonable to speculate that rinsing stents with high pressure before implantation may modify surface stent electrostatic forces and reduce stent interaction with circulating proteins.

Further, the solution used to rinse stents in this study contained a high concentration of heparin, thus potentially coating the stent with a thin layer of heparin immediately before implantation. A polyamine/dextran sulfate trilayer stent has been shown, in porcine arteries, to reduce thrombosis when heparin was covalently bound to the stent (Hardhammar, P. A., et al., 1996, *Circulation*, 93:423–430). This stent was used in the BENESTENT II trial (see Serruys, P. W., et al., 1996, *Circulation*, 93:412–422).

Although this study did not compare heparin-coated with non-coated stents, the results using this stent were favorable compared to historical controls. Doubt exists regarding the effectiveness of locally delivered heparin to reduce in-stent restenosis. In the pig restenosis model, heparin-coated stents have not shown a reduction in in-stent restenosis, as noted by Cox, D. A., et al., 1992, *Coronary Artery Dis*, 3:237–48.

This study also demonstrates that stent handling before implantation, even for only 10 sec hampers long-term results. Other investigators using mostly hand-crimped stents report similar evidence, as noted by Kornowski, R. et al., 1998, *J Am Coll Cardiol*, 31:224–30, and Rogers, C. et al., 1998, *Proc. Natl. Acad. Sci. USA*, 95:10134–10139.

Whelan et al described a significant reduction in the number of starch and textile fiber contaminants by modifying their practice to new revised implantation techniques which included measures such as frequent washing of glove hands, and minimal handling of catheters and guide wires (Rogers, C. et al., 1998, *Proc. Natl. Acad. Sci. USA*, 95:10134–10139).

In our study stent manual handling increased vessel percent stenosis by 15.3% compared to untouched stents, and by 35.9% compared to handled+rinsed stents. Vessel percent stenosis was reduced by 17.4% in untouched+rinsed stents compared to untouched stents. In absolute numbers the histomorphometric measurements were similar between these two groups, but a statistically significant reduction in neointimal thickness was observed when adjusted to arterial injury.

The above specification, data and examples provide an enabling description of the manufacture and use of the invention. Since many embodiments of the invention can be made without departing from the spirit and scope of the invention, the invention resides in the claims hereinafter appended.

We claim:

1. A stent treatment apparatus configured for use outside of a patient, comprising:

stent washing means for pressure washing a stent preloaded on a balloon catheter;

fluid inflow means for providing a washing fluid to the stent washing means;

fluid outflow means for removing the washing fluid from the stent washing means to a location outside of the patient; and receiving means for receiving a catheter within the stent washing apparatus.

2. The stent treatment apparatus of claim 1, wherein the stent washing means comprise a stent washing chamber.

3. The stent treatment apparatus of claim 2, wherein the fluid inflow means is in fluid communication with a first end of the stent washing chamber.

4. The stent treatment apparatus of claim 2, wherein the fluid outflow means is in fluid communication with a second end of the stent washing chamber.

5. The stent treatment apparatus of claim 1, wherein the washing fluid is provided from a pressurized source comprising a syringe or an indeflator.

6. The stent treatment apparatus of claim 1, wherein the wash fluid comprises a mixture of heparin and water.

7. The stent treatment apparatus of claim 1, wherein the fluid inflow means and the fluid outflow means are reversible between a closed position that does not permit fluid flow and an open position that does permit fluid flow.

8. The stent treatment apparatus of claim 1, further comprising pressure means for inflating inflate the balloon.

* * * * *